(12) United States Patent
Ouchi

(10) Patent No.: US 6,402,773 B1
(45) Date of Patent: Jun. 11, 2002

(54) TUBE CONNECTION STRUCTURE FOR ENDOSCOPE

(75) Inventor: Teruo Ouchi, Saitama-ken (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/506,806

(22) Filed: Feb. 18, 2000

(30) Foreign Application Priority Data

Feb. 25, 1999 (JP) .......................................... 11-047342

(51) Int. Cl.⁷ .............................................. A61B 17/28
(52) U.S. Cl. ...................................... 606/205; 285/334.5
(58) Field of Search ................................ 606/205, 207, 606/206, 208, 110, 1, 106, 108, 113; 285/371, 382, 398; 403/274, 281; 128/911, 912; 604/262, 533, 534, 538, 326

(56) References Cited

U.S. PATENT DOCUMENTS

| 3,734,106 A | * | 5/1973 | Zimmerman .............. 132/79 B |
| 4,114,930 A | * | 9/1978 | Perkins et al. ............ 285/334.5 |
| 5,217,002 A | | 6/1993 | Katsurada et al. |
| 5,846,184 A | * | 12/1998 | Corriveau et al. .......... 600/160 |
| 5,993,474 A | | 11/1999 | Ouchi |
| 6,013,095 A | | 1/2000 | Ouchi |

FOREIGN PATENT DOCUMENTS

| JP | 64-889 | 1/1989 |
| JP | 1-11258 | 3/1989 |

* cited by examiner

Primary Examiner—Henry J. Recla
Assistant Examiner—Vy Q. Bui
(74) Attorney, Agent, or Firm—Greenblum & Bernstein, P.L.C.

(57) ABSTRACT

A tube connection structure for endoscope system for connecting a flexible tube with a connection member is provided with a rigid cylindrical member tightly inserted in an end portion of the flexible tube. The connection member is provided with an opening for receiving the end portion of the flexible tube where the rigid cylindrical member is inserted. The size of the rigid cylindrical member is designed such that the flexible tube is tightly nipped between the rigid cylindrical member and an inner surface of the opening of the connection member.

8 Claims, 2 Drawing Sheets

TUBE CONNECTION STRUCTURE FOR ENDOSCOPE

BACKGROUND OF THE INVENTION

Figure 1:
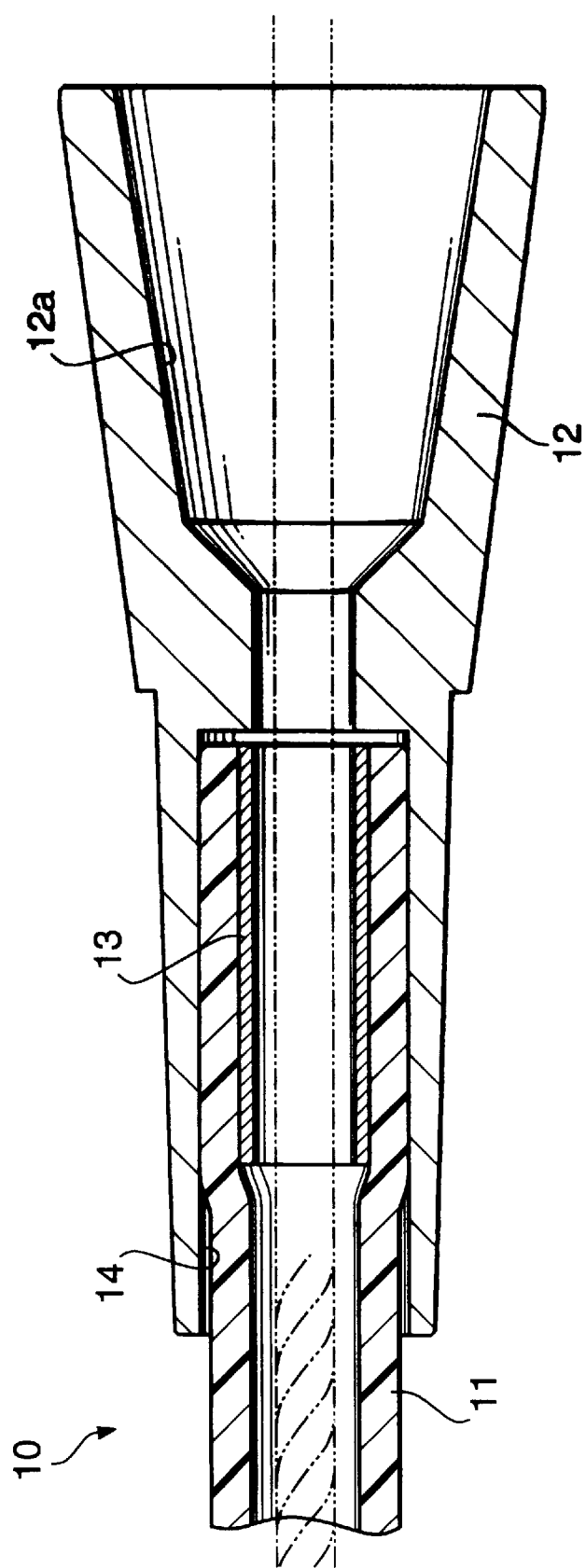

The present invention relates to a tube connection structure for endoscope, and particularly to a tube connection structure for connecting a flexible tube, which is used for endoscopes, treatment accessories and/or light source devices, with a connection member.

Conventionally, flexible tubes have been broadly used for endoscopes, treatment accessories and/or light source devices for endoscopes. Generally, one end of such a flexible tube is connected with a connection member.

A simple example known as a connection member is a pipe-shaped connection member, which is merely press-inserted in one end of a flexible tube. Another example is a connection member formed with an opening, in which one end of the flexible tube is merely inserted.

Further examples are: a connection member formed with a screw portion, which is screw-inserted in the end of the flexible tube; and a connection member having inside and outside tapered tubes which are screwed and engaged with each other, with the end of the flexible tube nipped therebetween.

In the former two examples, if the flexible tube is drawn strongly, the tube may be removed from the connection member. Therefore, such a structure should be used only in portions where the strong force may not be applied to the flexible tube.

In the latter two examples, since the structure includes a screw portion, whose diameter may be relatively large, positions where such a structure is used are limited.

SUMMARY OF THE INVENTION

It is therefore an object of the present invention to provided an improved tube connection structure for an endoscope to connect a flexible tube to a connection member, in which the connection part is not too thick, and enabling a sufficient connection strength.

For the above object, according to the present invention, there is provided a tube connection structure for an endoscope system for connecting a flexible tube with a connection member. The structure includes a rigid cylindrical member tightly inserted in an end portion of the flexible tube. The connection member is provided with an opening for receiving the end portion of the flexible tube in which the rigid cylindrical member is tightly inserted. The diameter of the rigid cylindrical member is designed such that the flexible tube is tightly nipped between the rigid cylindrical member and an inner surface of the opening of the connection member.

With this structure, the connection part will not become too thick, with enabling a sufficient connection strength between the flexible tube and the connection member.

Optionally, an outer diameter of the cylindrical member may be substantially constant at any position along the axis thereof, and an inner diameter of the opening may be substantially constant at any position along the axis thereof.

Further optionally, the inner diameter of the cylindrical member may be substantially equal to an inner diameter of the flexible tube.

In a particular case, a thickness of a wall of the cylindrical member is within a range of 0.05 mm through 0.3 mm.

Still optionally, the flexible tube may be a sheath of a treatment accessory for an endoscope.

Alternatively, the flexible tube may be a tube to be inserted in a forceps channel of an endoscope.

BRIEF DESCRIPTION OF THE ACCOMPANYING DRAWINGS

Figure 2:
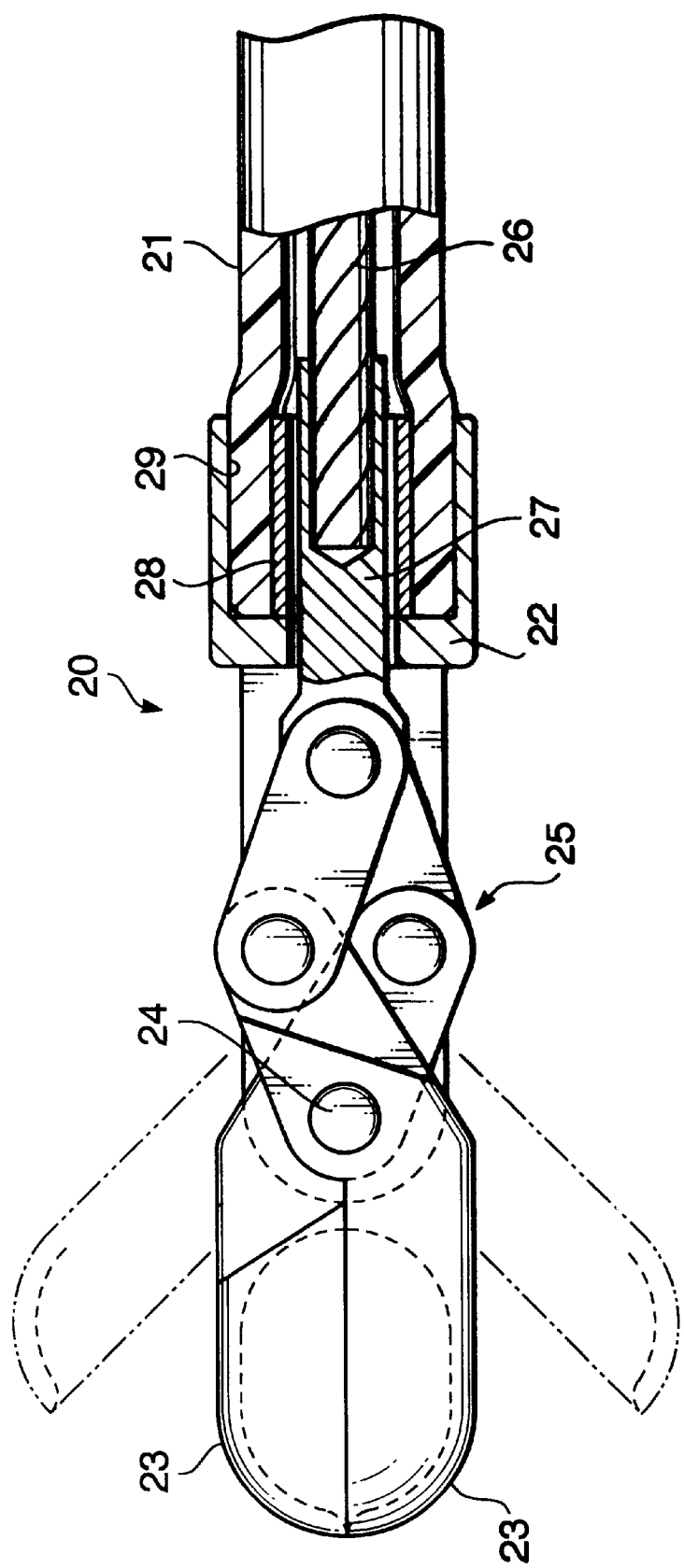

FIG. 1 is a cross-sectional side view, at a proximal end portion, of a catheter for an endoscope, according to a first embodiment of the invention; and FIG. 2 is a cross-sectional side view, at a distal end portion, of a biopsy forceps for an endoscope, according to a second embodiment of the invention.

DESCRIPTION OF THE EMBODIMENTS

Hereinafter, the present invention will be described with reference to the accompanying drawings.

FIG. 1 is a cross-sectional side view, at a proximal end portion, of a catheter 10 for an endoscope, according to a first embodiment of the invention. The catheter 10 is used for feeding contrast media, chromatophore agent and/or chemicals into a human cavity. When the catheter 10 is used for such purposes, it is inserted in a forceps channel of an endoscope (not shown).

In the embodiment, a flexible tube 11 is formed of tetrafluoroethylene, and the inner diameter is within a range between 0.5 mm through 2 mm, a thickness of a wall may be within a range of 0.2 mm through 0.5 mm, and an entire length of the flexible tube may be within a range of 0.5 m through 2 m.

At a proximal end of the flexible tube 11, a connection mouth 12 is connected. The connection mouth 12 is formed with a tapered opening 12a for receiving an injector (not shown). The connection mouth 12 is made of metal, rigid plastic, or the like.

As shown in FIG. 1, at an end portion of the flexible tube 11, a rigid pipe 13 made of stainless steel is press-inserted. Further, the end portion of the flexible tube 11 is press-inserted in a connection opening 14 formed on a cylindrical portion of the connection mouth 12.

An inner diameter of the rigid pipe 13 is substantially the same as the inner diameter of the flexible tube 11. Therefore, even though the rigid pipe 13 is inserted in the flexible tube 11, flow of liquid or the like through the flexible tube 11 is not affected by the rigid pipe 13. The thickness of the wall of the rigid pipe 13 is within a range of 0.05 mm through 0.2 mm. Thus, the outer diameter of the flexible tube 11 at a portion where the rigid pipe 13 is inserted has a thickness approximately twice as thick as the wall of the rigid pipe 13.

The connection opening 14 has a length which is longer than the length of the rigid pipe 13. The inner shape of the connection hole 14 is formed such that the flexible tube 11 can be freely inserted or removed without the rigid pipe 13, and when the rigid pipe 13 is inserted in the flexible tube 11, the flexible tube 11 is tightly inserted in the connection opening 14.

With the above structure, the proximal end of the flexible tube 11 is tightly nipped and crushed between the inner surface of the connection opening 14 and the rigid pipe 13. Accordingly, the flexible tube 11 is tightly connected with the connection mouth 12.

Even if the flexible tube 11 is drawn relatively strongly, it is not disconnected from the connection mouth 12 easily. Since the structure includes non-tapered surfaces (i.e., the outer surface of the rigid pipe 13 is substantially constant at any position along the axis thereof, and an inner diameter of the connection opening 14 is substantially constant at any position along the axis thereof) and the flexible tube located therebetween, the diameter of the connection mouth 12, and a compact structure can be realized.

It should be noted that the rigid pipe 13 and the connection opening 14 may have tapered portions which may be formed due to manufacturing necessity, such as a draft in molding process. In this specification, such a draft is considered to be non-tapered portion.

FIG. 2 shows a distal end portion of a biopsy forceps 20 for an endoscope. The biopsy forceps 20 has a sheath 21 that is a flexible tube formed of tetrafluoroethylene.

At a distal end of the flexible sheath 21, a connection member 22 is provided. To the connection member 22, a pair of biopsy cups 23 rotatably and openably supported about a supporting pin 24 are provided. Further, a link mechanism 25 for opening/closing the biopsy cups 23 is provided.

An operation wire 26, which slidably extends along the axis of the sheath 21, is connected to the link mechanism 25 via a connection rod 27. By operating the operation wire 26 at the proximal end of the endoscope, the biopsy cups 23 can be opened/closed.

Between the sheath 21 and the connection member 22, a connection structure similar to the first embodiment is employed. Specifically, inside the sheath 21, a cylindrical rigid pipe 28 made of stainless-steel is tightly inserted. Further, inside a connection opening 29 formed on a cylindrical portion of the connection member 22, the end of the flexible tube 11 is tightly inserted.

The inner diameter of the rigid pipe 28 is approximately the same as the inner diameter of the flexible sheath 21. The thickness of the wall of the rigid pipe 28 is within a range of 0.2 mm through 0.3 mm. In this embodiment, the depth (i.e., a length along the central axis) of the connection opening 29 is approximately the same as the length of the rigid pipe 28.

Further, the inner diameter of the connection opening 29 is designed such that the flexible sheath 21 is freely inserted without the rigid pipe 28, and that the flexible sheath 21 is tightly inserted when the rigid pipe 28 is inserted in the sheath 21.

With the above structure, the end portion of the sheath 21 is tightly nipped and crushed between the inner surface of the connection opening 29 and the rigid pipe 28, and the flexible sheath 21 is tightly connected with the connection member 22.

It should be noted that the invention is not limited to the structures described above, but can be applied for connecting a flexible tube to various connecting members for an endoscope, treatment accessories for an endoscope, and light source device for an endoscope.

The present disclosure relates to the subject matter contained in Japanese Patent Application No. HEI 11-047342, filed on Feb. 25, 1999, which is expressly incorporated herein by reference in its entirety.

What is claimed is:

1. A tube connection structure for an endoscope system, said structure connecting an end portion of a flexible tube with a connection member, said structure including a rigid cylindrical member positioned within the end portion of said flexible tube and in tight contact with said flexible tube, said connection member being provided with a portion having a cylindrical opening for receiving the end portion of said flexible tube, the connection member having an internal shoulder at an end of the portion having the cylindrical opening, an end of the flexible tube abutting against the shoulder, said rigid cylindrical member being configured such that the end portion of said flexible tube is tightly nipped and deformed between an outer surface of said rigid cylindrical member and an inner surface of said portion having the cylindrical opening of said connection member;

wherein, the entire length of the cylindrical member in the axial direction is positioned within the flexible tube.

2. The tube connection structure according to claim 1, wherein an outer diameter of said cylindrical member is substantially constant at any position along the axis thereof, and wherein an inner diameter of said portion having the cylindrical opening is substantially constant any position where the cylindrical member is received.

3. The tube connection structure according to claim 1, wherein inner diameter of said cylindrical member is substantially equal to an inner diameter of said flexible tube.

4. The tube connection structure according to claim 3, wherein a thickness of a wall of said cylindrical member is within a range of 0.05 mm through 0.3 mm.

5. The tube connection structure according to claim 1, wherein said flexible tube is a sheath of a treatment accessory for an endoscope.

6. The tube connection structure according to claim 1, wherein said flexible tube is a tube to be inserted in a forceps channel of an endoscope.

7. The tube connection structure for endoscope system according to claim 1, wherein, the rigid cylindrical member and the portion having the cylindrical opening directly contacts and holds the end of said flexible tube without any intervening member.

8. A tube connection structure for an endoscope system, said structure connecting a flexible tube with a connection member, said structure including a rigid cylindrical member positioned within an end portion of said flexible tube and in tight contact with said flexible tube, said connection member being provided with a portion having an opening for receiving the end portion of said flexible tube, said rigid cylindrical member being configured such that said flexible tube is tightly nipped between said rigid cylindrical member and an inner surface of said opening of said connection member, an axial length of the portion having the opening being longer than an axial length of the rigid cylindrical member;

wherein, the entire length of the cylindrical member in the axial direction is positioned within the flexible tube.

* * * * *